(12) United States Patent
Soon-Shiong

(10) Patent No.: US 12,180,492 B2
(45) Date of Patent: Dec. 31, 2024

(54) METHODS AND SYSTEMS FOR PRODUCING A PROTEIN OF INTEREST IN A PLANT

(71) Applicant: ImmunityBio, Inc., Culver City, CA (US)

(72) Inventor: Patrick Soon-Shiong, Los Angeles, CA (US)

(73) Assignee: ImmunityBio, Inc., Culver City, CA (US)

( * ) Notice: Subject to any disclaimer, the term of this patent is extended or adjusted under 35 U.S.C. 154(b) by 215 days.

(21) Appl. No.: 17/750,768

(22) Filed: May 23, 2022

(65) Prior Publication Data

US 2022/0396803 A1    Dec. 15, 2022

Related U.S. Application Data

(60) Provisional application No. 63/208,836, filed on Jun. 9, 2021.

(51) Int. Cl.
| | | |
|---|---|---|
| *C12N 15/82* | (2006.01) | |
| *A01H 3/02* | (2006.01) | |
| *C07K 14/54* | (2006.01) | |
| *C07K 14/715* | (2006.01) | |
| *C07K 16/46* | (2006.01) | |

(52) U.S. Cl.
CPC ........... *C12N 15/8258* (2013.01); *A01H 3/02* (2013.01); *C07K 14/5443* (2013.01); *C07K 14/7155* (2013.01); *C07K 16/46* (2013.01); *C12N 15/8251* (2013.01); *C07K 2317/52* (2013.01); *C07K 2319/30* (2013.01); *C07K 2319/32* (2013.01)

(58) Field of Classification Search
None
See application file for complete search history.

(56) References Cited

U.S. PATENT DOCUMENTS

| | | |
|---|---|---|
| 8,007,558 B2 | 8/2011 | Audet |
| 9,328,159 B2 | 5/2016 | Wong et al. |
| 10,358,478 B2 | 7/2019 | Wong et al. |
| 11,129,883 B2 | 9/2021 | Marcus et al. |
| 11,168,138 B2 | 11/2021 | Li et al. |
| 11,173,191 B2 | 11/2021 | Liu et al. |
| 2010/0251417 A1 | 9/2010 | D'Aoust et al. |
| 2013/0295609 A1 | 11/2013 | D'Aoust et al. |
| 2015/0218579 A1 | 8/2015 | D'Aoust et al. |
| 2015/0272076 A1 | 10/2015 | Mathis et al. |
| 2016/0326234 A1 | 11/2016 | Hiatt |
| 2017/0204427 A1 | 7/2017 | Michaud et al. |
| 2019/0300591 A1 | 10/2019 | Wong |
| 2019/0377946 A1* | 12/2019 | Genty ................... G06V 10/82 |
| 2021/0196821 A1 | 7/2021 | Wong et al. |

FOREIGN PATENT DOCUMENTS

| | | |
|---|---|---|
| CN | 106069748 B | 6/2018 |
| WO | WO-2002101006 A2 | 12/2002 |
| WO | WO-2005076766 A2 | 8/2005 |
| WO | WO-2006004675 A2 | 1/2006 |
| WO | WO-2016004060 A2 | 1/2016 |
| WO | WO-2018075989 A1 | 4/2018 |

OTHER PUBLICATIONS

Kamba et al. Journal of nanomaterials (2013) pp. 1-9.*
Werner et al. PNAS (2011)108(34):14061-14066.*
Homesteaders Backyarders (2019). Farm & Garden Catalog Animal Nutrition and Soil Amendments. 7, 31-37.
Amaya-Carpio L. et al. (2009). Arbuscular mycorrhizal fungi and organic fertilizer influence photosynthesis, root phosphatase activity, nutrition, and growth of Ipomoea carnea ssp. Fistulosa. International Journal for Photosynthesis Research, Kluwer Academic Publishers, 47(1): 1-10.
International Search Report from PCT/US2022/030473 dated Sep. 27, 2022.
Written Opinion from PCT/US2022/030473 dated Sep. 27, 2022.
Liu, B., et al., "Bifunctional TGF-B trap/IL-15 protein complex elicits potent NK cell and CD8+ T cell immunity against solid tumors," Molecular Therapy, 29(10): 2949-2962 (2021).

* cited by examiner

*Primary Examiner* — Medina A Ibrahim
(74) *Attorney, Agent, or Firm* — Harness Dickey & Pierce P.L.C.

(57) ABSTRACT

Methods and systems for producing a protein of interest within a plant or a portion of a plant are provided herein. The method includes introducing one or more nucleic acid into the plant or the portion of the plant, the nucleic acid including a nucleotide sequence encoding the protein of interest and incubating the plant or the portion of the plant under conditions that permit the expression of the nucleotide sequence encoding the protein of interest. The method also includes adding a medium amendment including a calcium carbonate source, such as aragonite, to a medium environment of the plant.

20 Claims, 6 Drawing Sheets

METHODS AND SYSTEMS FOR PRODUCING A PROTEIN OF INTEREST IN A PLANT

CROSS-REFERENCE TO RELATED APPLICATIONS

This application claims the benefit under 35 U.S.C. § 119(e) of U.S. Provisional Application No. 63/208,836, filed on Jun. 9, 2021. The entire disclosure of the provisional application is incorporated herein by reference in its entirety.

FIELD

Methods and systems for producing a protein of interest in a plant or a part of a plant are provided herein including providing a medium amendment, for example, including a calcium carbonate source including aragonite, to a medium environment, such as soil, of the plant.

BACKGROUND

The background description includes information that may be useful in understanding the systems and methods described herein. It is not an admission that any of the information provided herein is prior art, or that any publication specifically or implicitly referenced is prior art.

Transformation of plant tissues has emerged as an alternative mode of transgenesis that has created new opportunities for plant biotechnology in therapeutic protein production, metabolic engineering, and synthetic biology. For example, therapeutic protein production in plants is an area of great potential for increasing and improving the production of proteins for the treatment or prevention of disease in humans and other animals. Advantageously, various antibodies, vaccines, enzyme therapies and other therapeutic proteins can be produced in plant tissues.

Plant cells, unlike bacteria or yeast, can correctly fold, assemble and modify complex proteins of mammalian origin, such as therapeutic and diagnostic antibodies. Furthermore, in contrast to traditional mammalian cell culture, plant-based protein expression does not typically require development of high-producing cell lines to enable large-scale production. Rather than switching to larger bioreactors and the associate increased costs and complexity for scale-up of mammalian cell protein expression, scale-up of plant protein productions requires growing more plants. Thus, plant-based protein expression provides many benefits in terms of ease of scale-up, safety, and capital investment compared to mammalian cell-based production systems.

WO 2002/101006 (Icon Genetics) reports expressing proteins in plants, especially proteins that require the coordinate expression of a plurality of structural genes to become biologically active.

WO 2005/076766 (Sunol Molecular Corp.) reports transient expression of proteins in plants. Monoclonal antibodies and other pharmaceutically important proteins are expressed from transgenes transformed into the plants by Agrobacter delivery vectors.

WO 2006/004675 (Altor Bioscience Corp.) reports the production of human tissue factors in plants for treating disorders of the vasculatory system.

Thus, there is a need to optimize expression and increase the quantity and quality of protein production in plants, for example, via methods including addition of an amendment to the medium environment of the plant as well as modifying a duration of light and/or intensity of light supplied to the plant during growth.

SUMMARY

This section provides a general summary of the disclosure, and is not a comprehensive disclosure of its full scope or all of its features.

The present disclosure relates to methods and systems for producing a protein of interest within a plant or a portion of a plant. In various aspects, the present disclosure provides a method for producing a protein of interest within a plant or a portion of a plant. The method includes introducing one or more nucleic acid into the plant or the portion of the plant. The nucleic acid includes a nucleotide sequence encoding the protein of interest, and the nucleotide sequence is operatively linked to a regulatory region. For example, the nucleotide sequence encodes a pharmaceutically active protein, an antibody, an antigen, a vaccine, an enzyme or an industrial enzyme. The method further includes incubating the plant or the portion of the plant under conditions that permit the expression of the nucleotide sequence encoding the protein of interest, thereby producing the protein of interest, and adding a medium amendment to a medium environment, such as soil, of the plant. The medium amendment includes a calcium carbonate source including aragonite.

In various aspects, the present disclosure also provides a system for producing a protein of interest within a plant or a portion of a plant. The system includes a medium environment, such as soil, adapted to grow the plant. The medium environment includes a medium amendment including a calcium carbonate source including aragonite. The plant includes one or more nucleic acids introduced into the plant or the portion of the plant. The nucleic acid includes a nucleotide sequence encoding the protein of interest, and the nucleotide sequence is operatively linked to a regulatory region. For example, the nucleotide sequence encodes a pharmaceutically active protein, an antibody, an antigen, a vaccine, an enzyme or an industrial enzyme. The system further includes incubation equipment adapted to incubate the plant under conditions that permit the expression of the nucleotide sequence encoding the protein of interest, thereby producing the protein of interest. The incubation equipment includes at least one lighting element to supply light to the plant. The system may further include at least one sensor associated with a plant, the at least one sensor configured to sense at least one parameter of the plant, memory configured to store computer-executable instructions, and at least one processor configured to execute the instructions. The instructions include receiving the sensed at least one parameter of the plant. The instructions may also include at least one of: controlling operation of the lighting element to modify a duration of light supplied to the plant during one or more specified daily time periods, during growth of the plant, according to the sensed at least one parameter of the plant; controlling operation of the lighting element to modify an intensity of light supplied to the plant during growth of the plant, according to the sensed at least one parameter of the plant; and controlling operation of the lighting element to modify a wavelength of light supplied to the plant during growth of the plant, according to the sensed at least one parameter of the plant.

Various objects, features, aspects and advantages of the present subject matter will become more apparent from the following detailed description of preferred embodiments.

BRIEF DESCRIPTION OF DRAWINGS

In the drawings, reference numbers may be reused to identify similar and/or identical elements.

DETAILED DESCRIPTION

Figure 1:
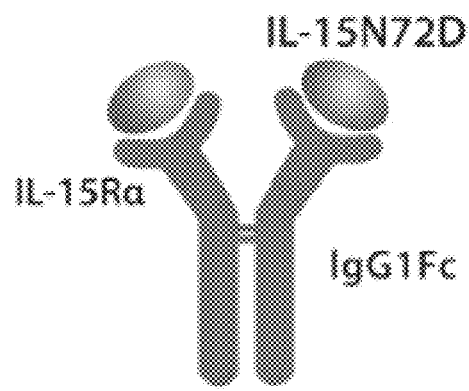
FIG. 1 is a representation of NAI (N-803).

All percentages and ratios are calculated by weight unless otherwise indicated. All percentages and ratios are calculated based on the total composition unless otherwise indicated.

All component or composition levels are in reference to the active level of that component or composition, and are exclusive of impurities, for example, residual solvents or byproducts, which may be present in commercially available sources.

I. Methods for Producing a Protein of Interest

Methods for producing a protein of interest in a plant or a portion of a plant are provided herein. A method includes introducing one or more nucleic acid into the plant or the portion of the plant, wherein the nucleic acid comprises a nucleotide sequence encoding the protein of interest. The method further includes incubating the plant or the portion of the plant under conditions that permit the expression of the nucleotide sequence encoding the protein of interest, thereby producing the protein of interest, and adding a soil amendment to a soil environment of the plant, wherein the soil amendment comprises a calcium carbonate source comprising aragonite.

As used herein, "portion of a plant" refers to any part derived from a plant, including tissue obtained from the plant, for example, but not limited to, the leaves, the leaves and stem, the roots, the aerial portion including the leaves, stem and optionally the floral portion of the plant, cells, protoplasts or any combination thereof obtained from the plant. For example, "portion of a plant" may refer to the leaves or stems of a plant.

As used herein, the term "plant matter" refers to any material derived from a plant. Plant matter may encompass an entire plant, tissue, cells, or any fraction thereof as well as intracellular plant components, extracellular plant components, liquid or solid extracts of plants, or a combination thereof. The term plant matter may also encompass plants, plant cells, tissue, a liquid extract, or a combination thereof, from plant leaves, stems, fruit, roots or a combination thereof. Plant matter may include a plant or portion thereof, which has not been subjected to any processing steps. Alternatively, it is also contemplated that plant matter may be subjected to minimal processing steps as defined below, or more rigorous processing, including partial or substantial protein purification using techniques commonly known within the art including, but not limited to, chromatography, electrophoresis, and the like.

A. Introducing One or More Nucleic Acid

As used herein, the term "nucleotide (or nucleic acid) sequence of interest" or "coding region of interest" refers to any nucleotide sequence, or coding region (these terms may be used interchangeably) that is to be expressed within a host organism, for example a plant, to produce a protein of interest. Such a nucleotide sequence of interest may encode, but is not limited to, native or modified proteins, an industrial enzyme or a modified industrial enzyme, an agricultural protein or a modified agricultural protein, a helper protein, a protein supplement, a pharmaceutically active protein, a nutraceutical, a value-added product, or a fragment thereof for feed, food, or both feed and food use.

In any embodiment, the nucleotide sequence encoding the protein of interest may be operatively linked to a regulatory region. As used herein, "regulatory region," "regulatory element," or "promoter" refer to a portion of nucleic acid typically, but not always, upstream of the protein coding region of a gene, which may be comprised of either DNA or RNA, or both DNA and RNA. Further, the term "regulatory element" or "regulatory region" typically refers to a sequence of DNA, usually, but not always, upstream (5') to the coding sequence of a structural gene, which controls the expression of the coding region by providing the recognition for RNA polymerase and/or other factors required for transcription to start at a particular site. However, it is to be understood that other nucleotide sequences, located within introns, or 3' of the sequence may also contribute to the regulation of expression of a coding region of interest. An example of a regulatory element that provides for the recognition for RNA polymerase or other transcriptional factors to ensure initiation at a particular site is a promoter element.

As used herein, "operatively linked" means the particular sequences interact either directly or indirectly to carry out an intended function, such as mediation or modulation of gene expression. The interaction of operatively linked sequences may, for example, be mediated by proteins that interact with the operatively linked sequences. A transcriptional regulatory region and a sequence of interest are operably linked when the sequences are functionally connected so as to permit transcription of the sequence of interest to be mediated or modulated by the transcriptional regulatory region.

When a regulatory region is active, and in operative association, or operatively linked, with a gene of interest, this may result in expression of the gene of interest. A regulatory element may be capable of mediating organ specificity, or controlling developmental or temporal gene activation. A "regulatory region" includes promoter elements, core promoter elements exhibiting a basal promoter activity, elements that are inducible in response to an external stimulus, elements that mediate promoter activity such as negative regulatory elements or transcriptional enhancers.

"Regulatory region," as used herein, also encompasses elements that are active following transcription, for example, regulatory elements that modulate gene expression such as translational and transcriptional enhancers, translational and transcriptional repressors, upstream activating sequences, and mRNA instability determinants. Several of these latter elements may be located proximal to the coding region.

Most, but not all, eukaryotic promoter elements contain a TATA box, a conserved nucleic acid sequence comprised of adenosine and thymidine nucleotide base pairs usually situated approximately 25 base pairs upstream of a transcriptional start site. A promoter element comprises a basal promoter element, responsible for the initiation of transcription, as well as other regulatory elements (as listed above) that modify gene expression.

A constitutive regulatory region directs the expression of a gene throughout the various parts of a plant and continuously throughout plant development. Examples of known constitutive regulatory elements include promoters associated with the CaMV 35S transcript. (Odell et al., 1985, Nature, 313: 810-812), the rice actin 1 (Zhang et al, 1991, Plant Cell, 3: 1155-1165), actin 2 (An et al, 1996, Plant J., 10: 107-121), or tms 2 (U.S. Pat. No. 5,428,147, which is incorporated herein by reference in its entirety), and triosephosphate isomerase 1 (Xu et. al., 1994, Plant Physiol. 106: 459-467) genes, the maize ubiquitin 1 gene (Cornejo et al, 1993, Plant Mol. Biol. 29: 637-646), the Arabidopsis ubiquitin 1 and 6 genes (Holtorf et al, 1995, Plant Mol. Biol. 29: 637-646), and the tobacco translational initiation factor 4A gene (Mandel et al, 1995 Plant Mol. Biol. 29: 995-1004). The term "constitutive" as used herein does not necessarily indicate that a gene under control of the constitutive regulatory region is expressed at the same level in all cell types, but that the gene is expressed in a wide range of cell types even though variation in abundance is often observed.

In an embodiment, the one or more nucleic acid may be introduced into the plant or a portion of the plant by methods known in the art. For example, one or more nucleic acid can be introduced into plant cells using Ti plasmids, Ri plasmids, plant virus vectors, direct DNA transformation, micro-injection, electroporation, etc. For reviews of such techniques, see for example, Weissbach and Weissbach, Methods for Plant Molecular Biology, Academy Press, New York VIII, pp. 421-463 (1988); Geierson and Corey, Plant Molecular Biology, 2d Ed. (1988); and Miki and Iyer, Fundamentals of Gene Transfer in Plants. In Plant Metabolism, 2d Ed. D T. Dennis, D H Turpin, D D Lefebrve, D B Layzell (eds), Addison Wesly, Langmans Ltd. London, pp. 561-579 (1997). Other methods include direct DNA uptake, the use of liposomes, electroporation, for example using protoplasts, micro-injection, microprojectiles or whiskers, and vacuum infiltration. See, for example, Bilang, et al. (1991, Gene 100: 247-250), Scheid et al. (1991, Mol. Gen. Genet. 228: 104-112), Guerche et al. (1987, Plant Science 52: 111-116), Neuhause et al. (1987, Theor. Appl Genet. 75: 30-36), Klein et al., (2987, Nature 327: 70-73); Freeman et al. (1984, Plant Cell Physiol. 29: 1353), Howell et al. (1980, Science 208: 1265), Horsch et al. (1985, Science 227: 1229-1231), DeBlock et al., (1989, Plant Physiology 91: 694-701), Methods for Plant Molecular Biology (Weissbach and Weissbach, eds., Academic Press Inc., 1988), Methods in Plant Molecular Biology (Schuler and Zielinski, eds., Academic Press Inc., 1989), WO 92/09696, WO 94/00583, EP 331083, EP 175966, Liu and Lomonossoff (2002, J Virol Meth, 105:343-348), EP 290395; WO 8706614; U.S. Pat. Nos. 4,945,050; 5,036,006; 5,100,792; 5,625,136; and 6,403,865 (all of which are hereby incorporated herein by reference in their entirety).

"Expression cassette" refers to a nucleotide sequence comprising a nucleic acid of interest under the control of, and operably (or operatively) linked to, an appropriate promoter or other regulatory elements for transcription of the nucleic acid of interest in a host cell, for example a plant cell.

B. Incubating the Plant or Portion of the Plant

The method includes incubating the plant or the portion of the plant under conditions that permit the expression of the nucleotide sequence encoding the protein of interest, thereby producing the protein of interest. Incubation conditions may include, for example, duration of light exposure, temperature, light intensity, light wavelength, watering schedule, humidity level, etc. For example, suitable incubation conditions for a plant or portion of a plant may include one or more of: about 30-90 days (e.g., 30 days, 60 days, 90 days) at about 60° F. to about 85° F. (e.g., about 65° F., about 70° F., 80° F.) in a daily light cycle (e.g. photoperiod) of 12 hours on 12 hours off, a light intensity of about 20 $\mu mol/m^2s$ to about 2300 $\mu mol/m^2s$ (e.g, about 50 $\mu mol/m^2s$, about 100 $\mu mol/m^2s$, about 120 $\mu mol/m^2s$, about 150 $\mu mol/m^2s$, about 250 $\mu mol/m^2s$, about 500 $\mu mol/m^2s$, about 1000 $\mu mol/m^2s$, about 1500 $\mu mol/m^2s$, about 2000 $\mu mol/m^2s$), light wavelength of about 400 nm to about 700 nm (e.g. about 450 nm, about 500 nm, about 600 nm, about 650 nm) and about 30% to about 70% humidity (e.g., about 50%, about 60%, about 65%). Suitable incubation conditions may change depending on the type, condition, developmental stage, etc. of the plant or portion of the plant.

In any embodiment, the nucleic acid may be transiently expressed in the plant. As used herein, the term "transient expression" or "transiently expressed" refers to expression of a nucleic acid that has not been integrated into the plant cell's genome. Transient expression usually results in short-term expression and rapid results. Transient expression methods may be used to express the constructs of the present invention (see D'Aoust et al., 2009, Methods in molecular biology, Vol 483, pages 41-50; Liu and Lomonossoff, 2002, Journal of Virological Methods, 105:343-348; which is incorporated herein by reference in its entirety). Alternatively, a vacuum-based transient expression method, as described by Kapila et al., (1997, Plant Sci. 122, 101-108; which is incorporated herein by reference in its entirety), or WO 00/063400, WO 00/037663 (which are incorporated herein by reference in their entirety) may be used. These methods may include, but are not limited to, a method of agroinoculation or agroinfiltration, syringe infiltration, however, other transient methods may also be used as noted above. With agroinoculation, agroinfiltration, or syringe infiltration, a mixture of Agrobacteria comprising the desired nucleic acid enter the intercellular spaces of a tissue, for example the leaves, aerial portion of the plant (including stem, leaves and flower), other portion of the plant (stem, root, flower), or the whole plant. After crossing the epidermis the Agrobacteria infect and transfer t-DNA copies into the cells. The t-DNA is episomally transcribed and the mRNA translated, leading to the production of the protein of interest in infected cells, however, the passage of t-DNA inside the nucleus is transient.

If a plant, a plant portion, or a plant cell are to be transformed or co-transformed by two or more nucleic acids, the nucleic acids may be introduced into the Agrobacterium in a single transfection event where the nucleic acids are pooled, and the bacterial cells transfected as described. Alternately, each nucleic acid may be introduced serially. In this case, a first nucleic acid may be introduced to the *Agrobacterium* as described, the cells grown under selective conditions (e.g., in the presence of an antibiotic) where only the singly transformed bacteria can grow. Following this first selection step, a second nucleic acid can be introduced to the *Agrobacterium* as described, and the cells grown under doubly-selective conditions, where only the doubly-transformed bacteria can grow. The doubly-transformed bacteria may then be used to transform a plant, plant portion or plant cell as described herein, or may be subjected to a further transformation step to accommodate a third nucleic acid.

Alternatively, if plants, a plant portion, or a plant cell are to be transformed or co-transformed by two or more nucleic acids, the nucleic acids may be introduced into the plant by co-infiltrating a mixture of *Agrobacterium* cells with the plant, plant portion, or plant cell, each *Agrobacterium* cell may comprise one or more nucleic acids to be introduced within the plant. In order to vary the relative expression levels within the plant, plant portion or plant cell, of a nucleotide sequence of interest within a construct, during the step of infiltration, the concentration of the various Agrobacteria populations comprising the desired constructs may be varied.

Additionally or alternatively, the protein of interest may be expressed in an expression system that comprises amplification elements and/or regulatory elements or regions (also referred to herein as enhancer elements). As used herein, the term "amplification elements" refers to a nucleic acid segment comprising at least a portion of one or more long intergenic regions (LIR) of a geminivirus genome. As used herein, "long intergenic region" refers to a region of a long intergenic region that contains a rep binding site capable of mediating excision and replication by a geminivirus Rep protein. In some aspects, the nucleic acid segment comprising one or more LIRs, may further comprise a short intergenic region (SIR) of a geminivirus genome. As used herein, the term "short intergenic region" refers to the complementary strand (the short IR (SIR)) of a Mastreviruses). Any suitable geminivirus-derived amplification element may be used herein. See, for example, WO2000/20557; WO2010/025285; Zhang X. et al. (2005, *Biotechnology and Bioengineering*, Vol. 93, 271-279), Huang Z. et al. (2009, *Biotechnology and Bioengineering*, Vol. 103, 706-714), Huang Z. et al. (2009, *Biotechnology and Bioengineering*, Vol. 106, 9-17); which are herein incorporated by reference in their entirety). If more than one LIR is used in the construct, for example two LIRs, then the promoter, CMPV-HT regions and the nucleic acid sequence of interest and the terminator may be bracketed by each of the two LIRs For example, an amplification element from a geminivirus such as for example, an amplification element from the bean yellow dwarf virus (BeYDV) may be used to express the protein of interest. BeYDV belongs to the Mastreviruses genus adapted to dicotyledonous plants. BeYDV is monopartite having a single-strand circular DNA genome and can replicate to very high copy numbers by a rolling circle mechanism. BeYDV-derived DNA replicon vector systems have been used for rapid high-yield protein production in plants.

Additionally or alternatively, enhancer elements may be used to achieve a higher level of transient expression of the protein of interest. Enhancer elements may be based on RNA plant viruses, including comoviruses, such as Cowpea mosaic virus (CPMV; see, for example, WO2007/135480; WO2009/087391; US 2010/0287670, Sainsbury F. et al., 2008, *Plant Physiology;* 148: 121-1218; Sainsbury F. et al., 2008, *Plant Biotechnology Journal;* 6: 82-92; Sainsbury F. et al., 2009, *Plant Biotechnology Journal;* 7: 682-693; Sainsbury F. et al. 2009, *Methods in Molecular Biology*, Recombinant Proteins From Plants, vol. 483: 25-39; each of which are incorporated herein in their entirety), "CPMV HT+" as described in U.S. 61/971,274, which is incorporated herein by reference in its entirety or "CPMVX" (also referred as "CPMV 160") and/or "CPMVX+" (also referred to as "CPMV 160+") as described in U.S. 61/925,852, which is incorporated herein by reference in its entirety.

Post-transcriptional gene silencing (PTGS) may be involved in limiting expression of transgenes in plants, and co-expression of a suppressor of silencing from the potato virus Y (HcPro) may be used to counteract the specific degradation of transgene mRNAs (Brigneti et al., 1998, *EMBO J.* 17, 6739-6746, which is incorporated herein by reference in its entirety). Alternate suppressors of silencing are well known in the art and may be used as described herein (Chiba et al., 2006, *Virology* 346:7-14; which is incorporated herein by reference in its entirety), for example but not limited to, TEV-p1/HC-Pro (Tobacco etch virus-p1/HC-Pro), BYV-p21, p19 of Tomato bushy stunt virus (TBSV p19; the construction of p19 is described in described in WO 2010/0003225, which is incorporated herein by reference in its entirety), capsid protein of Tomato crinkle virus (TCV-CP), 2b of Cucumber mosaic virus; CMV-2b), p25 of Potato virus X (PVX-p25), p11 of Potato virus M (PVM-p11), p11 of Potato virus S (PVS-p11), p16 of Blueberry scorch virus, (BScV-p16), p23 of Citrus tristeza virus (CTV-p23), p24 of Grapevine leafroll-associated virus-2, (GLRaV-2 p24), p10 of Grapevine virus A, (GVA-p10), p14 of Grapevine virus B (GVB-p14), p10 of Heracleum latent virus (HLV-p10), or p16 of Garlic common latent virus (GCLV-p16).

One or more suppressors of silencing, include, but not limited to, HcPro, TEV-p1/HC-Pro, BYV-p21, TBSV p19, TCV-CP, CMV-2b, PVX-p25, rgscam, B2 protein from FHV, the small coat protein of CPMV, and coat protein from TCV, PVM-p11, PVS-p11, BScV-p16, CTV-p23, GLRaV-2 p24, GBV-p14, HLV-p10, GCLV-p16, or GVA-p10 may be co-expressed along with the comovirus-based expression cassette, geminivirus-derived amplification element, and the nucleic acid sequence encoding the protein of interest to further ensure high levels of protein production within a plant.

Alternatively, the nucleic acid may be stably expressed in the plant. As used herein, the term "stable expression" or "stably expressed" refers to expression of nucleic acid that has been integrated into the plant cell's genome. When nucleic acid is integrated into the genome, the nucleic acid can be passed to future generations. Stable expression usually results in long-term expression of the integrated nucleic acid. As most transformations start out as transient, the frequency of nucleic acid integration into the genome resulting in stable transformation is low. Stable expression may require more complex transformation techniques. For example, after nucleic acid is transferred into the cell and integrated into the genome, another step is often necessary to select for the stably transformed plants or plant cells and regeneration of whole viable plants. Alterations to plant regeneration techniques as well as nucleic acid transfer and integration techniques may be made via incubation conditions, type of transformation vector, etc. For example, desiccation of wheat plant tissue after *Agrobacterium* infection has resulted in T-DNA delivery enhancement, thus increasing frequency of stable transformation (see Cheng, M., Hu, T., Layton, J. et al., 2003, *In Vitro Cell Dev Biol-Plant*, Vol 39, pages 595-604; which is incorporated herein by reference in its entirety).

In any embodiment, the protein of interest may comprise a native, or a non-native signal peptide; the non-native signal peptide may be of plant origin. For example, the signal peptide may be a protein disulfide isomerase signal peptide (PDI). The native signal peptide may correspond to that of the protein of interest being expressed. The nucleotide sequence of interest, or coding region of interest may also include a nucleotide sequence that encodes a protein of interest, such as a pharmaceutically active protein, for example growth factors, growth regulators, antibodies, antigens, a vaccine, and fragments thereof, or their derivatives useful for immunization or vaccination and the like, an enzyme, and an industrial enzyme. Such proteins include, but are not limited to a protein that is a human pathogen, a viral protein, for example but not limited to one or more proteins from Respiratory syncytial virus (RSV), Rotavirus, influenza virus, human immunodeficiency virus (HIV), Rabies virus, human papilloma virus (HPV), Enterovirus 71 (EV71), or interleukins, for example one or more than one of IL-1 to IL-24, IL-26 and IL-27, cytokines, Erythropoietin (EPO), insulin, G-CSF, GM-CSF, hPG-CSF, M-CSF or combinations thereof, interferons, for example, interferon-alpha, interferon-beta, interferon-gamma, blood clotting factors, for example, Factor VIII, Factor IX, or tPA hGH, receptors, receptor agonists, antibodies for example but not limited to Rituxan, neuropolypeptides, insulin, vaccines, growth factors for example but not limited to epidermal growth factor, keratinocyte growth factor, transformation growth factor, growth regulators, antigens, autoantigens, fragments thereof, or combinations thereof.

The protein of interest may also include an influenza hemagglutinin (HA; see WO 2009/009876, which is incorporated herein by reference in its entirety). HA is a homotrimeric membrane type I glycoprotein, generally comprising a signal peptide, an HA1 domain, and an HA2 domain comprising a membrane-spanning anchor site at the C-terminus and a small cytoplasmic tail. Nucleotide sequences encoding HA are well known and are available (see, for example, the BioDefense and Public Health Database (Influenza Research Database; Squires et al., 2008 *Nucleic Acids Research* 36:D497-D503) at URL: biohealthbase.org/GSearch/home.do?decorator=Influenza; or the databases maintained by the National Center for Biotechnology Information (see URL: ncbi.nlm.nih.gov).

Additionally or alternatively, the protein of interest may be nogapendekin-alfa-inbakicept (NAI), also known as N-803 or ALT-803. NAI is an IL-15 superagonist complex comprising the IL-15N72D derivative bound to an IL-15Rα/IgG1 Fc fusion protein and can be seen in FIG. 1. U.S. Pat. No. 9,328,159 describes NAI and is incorporated herein by reference in its entirety.

Figure 2:
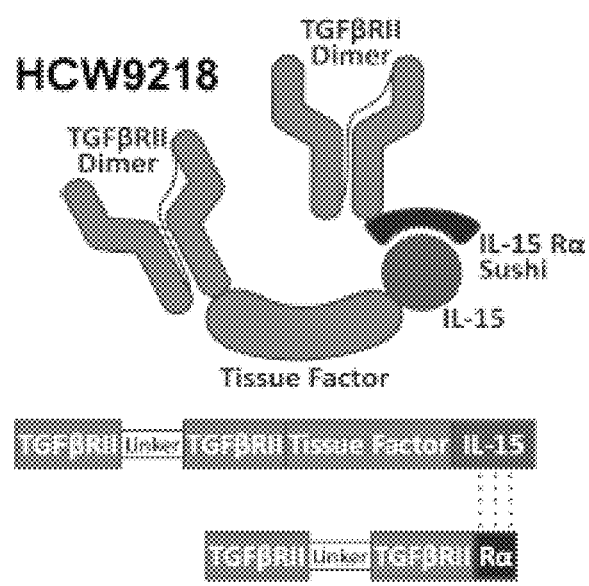
FIG. 2 is a representation of HCW9218.

Additionally or alternatively, the protein of interest may be a heterodimeric bifunctional fusion complex comprising a soluble TGF-βRII domain and an IL-15/IL15RαSu domain linked by a tissue factor linker. The molecule is also known as HCW9218. The molecule can be seen in FIG. 2. In another embodiment, the protein of interest is an IL-15D8N mutant form of HCW9218, which lacks IL-15 activity while exhibiting a TGF-β1 neutralizing activity similar to HCW9218. Both HCW9218 and HCW9228 are described in Liu, et al., 2021, *Mol. Ther.*, Vol. 29, pages 2949-2962, which is incorporated herein by reference in its entirety.

Figure 3:
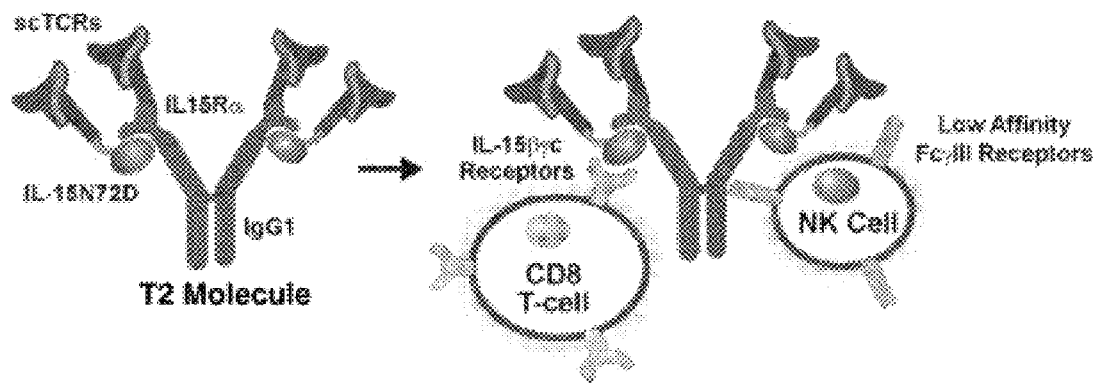
FIG. 3 is a representation of a fusion protein complex of an anti-CD20 single chain antibody and an IL-15 derivative IL-15N72D and the IL-15RαSu/IgG1 Fc fusion protein.

Additionally or alternatively, the protein of interest may be a soluble fusion protein comprising the C-terminal end of an anti-CD20 single chain antibody to the N-termini of an IL-15 derivative IL-15N72D and the IL-15RαSu/IgG1 Fc fusion protein. The protein is shown in FIG. 3. U.S. Pat. No. 10,358,478 describes the fusion protein, and is incorporated herein by reference in its entirety.

Figure 4:
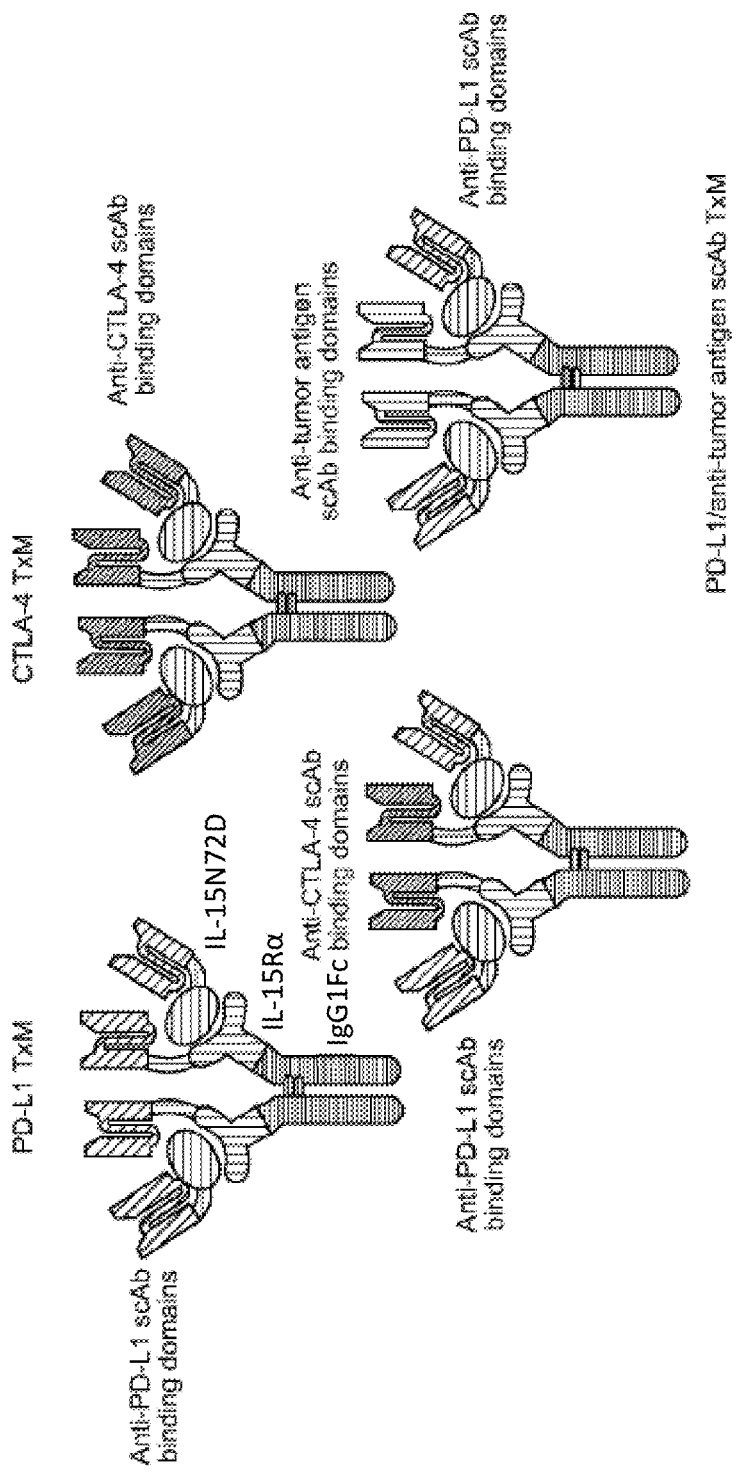
FIG. 4 is a schematic diagram illustrating different T×M complexes comprising the IL-15/IL-15RαSu/Fc scaffold fused to binding domains that recognize immune checkpoint molecules, immune signaling molecule and/or disease antigens.

Additionally or alternatively, the protein of interest may be one or more T×M. The term "T×M" refers to a complex comprising an IL-15N72D:IL-15RαSu/Fc scaffold linked to a binding domain. An exemplary T×M is an IL-15N72D:IL-15RαSu complex comprising a fusion to a binding domain that specifically recognizes PD-L1 (PD-L1 T×M). FIG. 4 is a schematic diagram illustrating different T×M complexes comprising the IL15/IL-15RαSu/Fc scaffold fused to binding domains that recognize immune checkpoint molecules, immune signaling molecule and/or disease antigens. WO 2018/075989, US 2021/0196821, and U.S. Pat. No. 11,173,191 describe T×Ms and are incorporated herein by reference in their entirety.

Figure 5A:
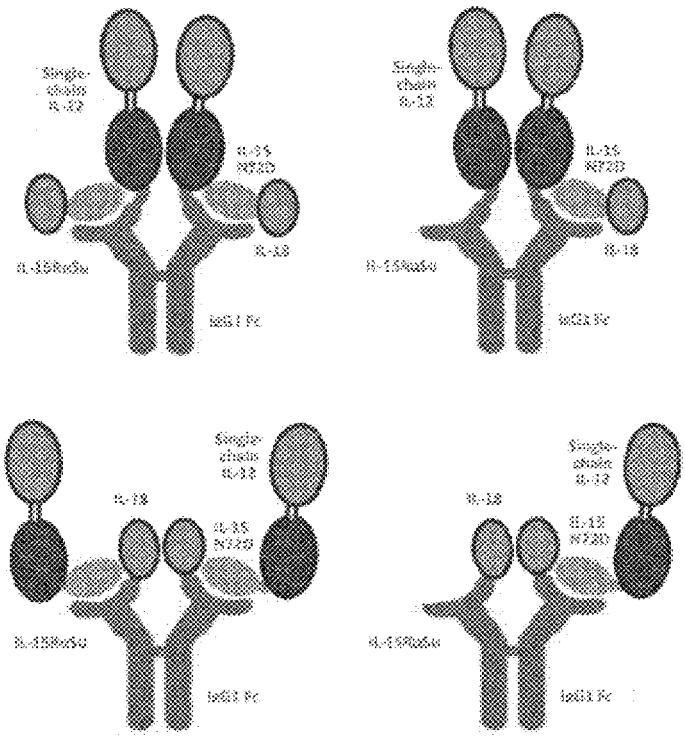
FIGS. 5A and 5B depict schematic diagrams of different T×M complexes comprising the IL-15N72D:IL-15RαSu scaffold fused to a binding domain of IL-12 and IL-18 (FIG. 5A) or a binding domain of IL-18 alone (FIG. 5B).
Figure 5B:
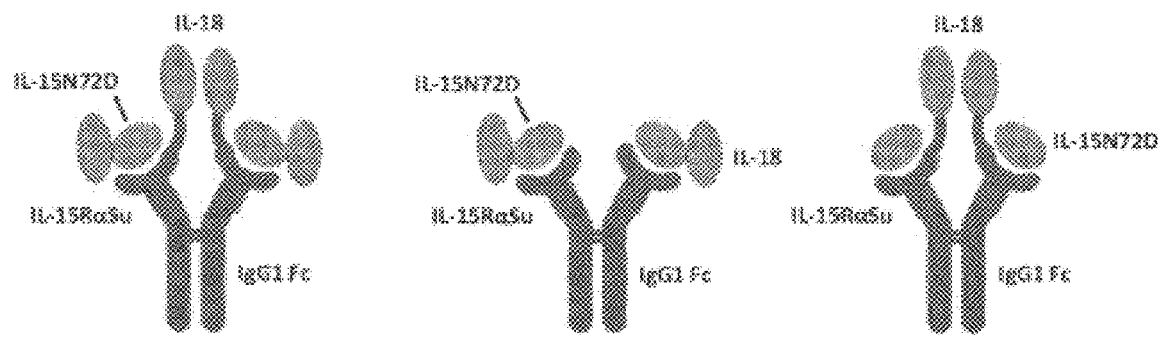

Additionally or alternatively, the binding domain of the T×M may be an IL-12 or an IL-18 binding domain. Examples of a T×M fusion complex comprising an IL-15N72D:IL-15RαSu scaffold fused to an IL-12 or IL-18 binding domain or only an IL-18 binding domain are shown in FIGS. 5A and 5B, respectively, and are described in U.S. Pat. No. 11,129,883, which is incorporated herein by reference in its entirety.

Figure 6:
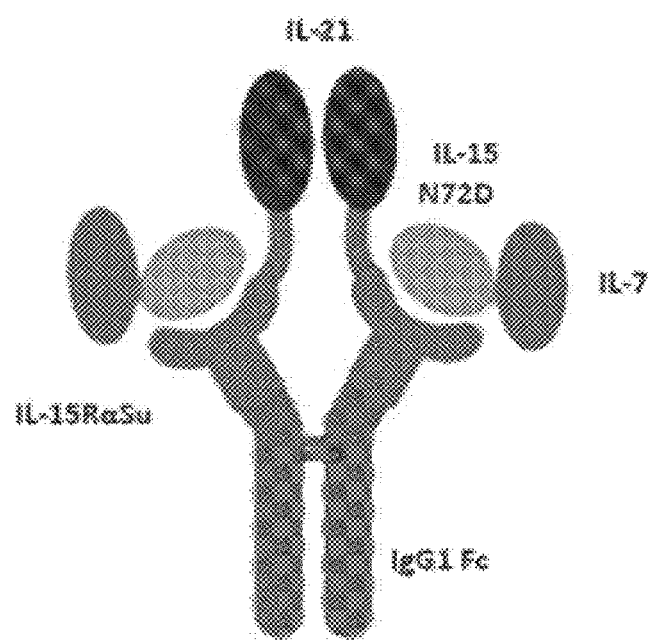
FIG. 6 is a schematic diagram of a T×M complex comprising the IL-15N7D:IL-15RαSu scaffold fused to IL-7 and IL-21.

Additionally or alternatively, the binding domain of the T×M may be an IL-7 and an IL-21 binding domain. Examples of a T×M fusion complex comprising an IL-15N72D:IL-15RαSu scaffold fused to an IL-7 or IL-21 binding domain are shown in FIG. 6, and are described in US 2019/0300591, which is incorporated herein by reference in its entirety.

Additionally or alternatively, the binding domain of the T×M may be a cytokine receptor, cytokine receptor, cytokine ligand, disease-specific antigen, immune checkpoint molecule, or immune signaling molecule. For example, the binding domain may be or bind to PD-1, PD-L1 CTLA-4, CD47, TIM-3, TNFR, GITR, ssDNA, HER2, EGFR, CD19, CD38, CD52, GD2, CD33, Notch 1, ICAM-1, tissue factor, or HIV envelope. The binding domain may be fused to the IL-15N72D:IL-15RαSu scaffold. Examples of such T×Ms are described in U.S. Pat. No. 11,168,138, which is incorporated herein by reference in its entirety.

Additionally or alternatively, the protein of interest may be a monoclonal antibody (mAb or moAb), for example, antibodies as described in WO 2016/004060, which is incorporated herein by reference in its entirety. Examples of mAbs include, but are not limited to, rituximab, ofatumumab, and obinutuzumab (anti-CD20 Abs); trastuzumab and pertuzumab (anti-HER2 Abs); cetuximab and panitumumab (anti-EGFR Abs); alemtuzumab (antiCD52 Ab); TA99 (mouse IgG2a). Other mAbs include, but are not limited to, nivolumab (anti-PD-1 Ab), TA99 (anti-gp75), 3F8 (anti-GD2), 8H9 (anti-B7-H3), abagovomab (anti-CA-125 (imitation)), adecatumumab (anti-EpCAM), afutuzumab (anti-CD20), alacizumab pegol (anti-VEGFR2), altumomab pentetate (anti-CEA), amatuximab (anti-mesothelin), AME-133 (anti-CD20), anatumomab mafenatox (anti-TAG-72), apolizumab (anti-HLA-DR), arcitumomab (anti-CEA), bavituximab (anti-phosphatidylserine), bectumomab (anti-CD22), belimumab (anti-BAFF), besilesomab (anti-CEA-related antigen), bevacizumab (anti-VEGF-A), bivatuzumab mertansine (anti-CD44 v6), blinatumomab (anti-CD19), BMS-663513 (anti-CD137), brentuximab vedotin (anti-CD30 (TNFRSF8)), cantuzumab mertansine (anti-mucin CanAg), cantuzumab ravtansine (anti-MUC1), capromab pendetide (anti-prostatic carcinoma cells), carlumab (anti-MCP-1), catumaxomab (anti-EpCAM, CD3), cBR96-doxorubicin immunoconjugate (anti-Lewis-Y antigen), CC49 (anti-TAG-72), cedelizumab (anti-CD4), Ch.14.18 (anti-GD2), ch-TNT (anti-DNA associated antigens), citatuzumab bogatox (anti-EpCAM), cixutumumab (anti-IGF-1 receptor), clivatuzumab tetraxetan (anti-MUC1), conatumumab (anti-TRAIL-R2), CP-870893 (anti-CD40), dacetuzumab (anti-CD40), daclizumab (anti-CD25), dalotuzumab (anti-insulin-like growth factor I receptor), daratumumab (anti-CD38 (cyclic ADP ribose hydrolase)), demcizumab (anti-DLL4), detumomab (anti-B-lymphoma cell), drozitumab (anti-DR5), duligotumab (anti-HER3), dusigitumab (anti-ILGF2), ecromeximab (anti-GD3 ganglioside), edrecolomab (anti-EpCAM), elotuzumab (anti-SLAMF7), elsilimomab (anti-IL-6), enavatuzumab (anti-TWEAK receptor), enoticumab (anti-DLL4), ensituximab (anti-5AC), epitumomab cituxetan (anti-episialin), epratuzumab (anti-CD22), ertumaxomab (anti-HER2/neu, CD3), etaracizumab (anti-integrin $\alpha v\beta 3$), faralimomab (anti-Interferon receptor), farletuzumab (anti-folate receptor 1), FBTA05 (anti-CD20), ficlatuzumab (anti-HGF), figitumumab (anti-IGF-1 receptor), flanvotumab (anti-TYRP1 (glycoprotein 75)), fresolimumab (anti-TGF (3), futuximab (anti-EGFR), galiximab (anti-CD80), ganitumab (anti-IGF-I), gemtuzumab ozogamicin (anti-CD33), girentuximab (anti-carbonic anhydrase 9 (CA-IX)), glembatumumab vedotin (anti-GPNMB), guselkumab (anti-IL13), ibalizumab (anti-CD4), ibritumomab tiuxetan (anti-CD20), icrucumab (anti-VEGFR-1), igovomab (anti-CA-125), IMAB362 (anti-CLDN18.2), IMC-CS4 (anti-CSFIR), IMC-TR1 (TGF RII), imgatuzumab (anti-EGFR), inclacumab (anti-selectin P), indatuximab ravtansine (anti-SDC1), inotuzumab ozogamicin (anti-CD22), intetumumab (anti-CD51), ipilimumab (anti-CD152), iratumumab (anti-CD30 (TNFRSF8)), KM3065 (anti-CD20), KW-0761 (anti-CD194), LY2875358 (anti-MET) labetuzumab (anti-CEA), lambrolizumab (anti-PDCD1), lexatumumab (anti-TRAIL-R2), lintuzumab (anti-CD33), lirilumab (anti-KIR2D), lorvotuzumab mertansine (anti-CD56), lucatumumab (anti-CD40), lumiliximab (anti-CD23 (IgE receptor)), mapatumumab (anti-TRAIL-R1), margetuximab (anti-ch4D5), matuzumab (anti-EGFR), mavrilimumab (anti-GMCSF receptor a-chain), milatuzumab (anti-CD74), minretumomab (anti-TAG-72), mitumomab (anti-GD3 ganglioside), mogamulizumab (anti-CCR4), moxetumomab pasudotox (anti-CD22), nacolomab tafenatox (anti-C242 antigen), naptumomab estafenatox (anti-5T4), narnatumab (anti-RON), necitumumab (anti-EGFR), nesvacumab (anti-angiopoietin 2), nimotuzumab (anti-EGFR), nivolumab (anti-IgG4), nofetumomab merpentan, ocrelizumab (anti-CD20), ocaratuzumab (anti-CD20), olaratumab (anti-PDGF-R a), onartuzumab (anti-c-MET), ontuxizumab (anti-TEM1), oportuzumab monatox (anti-EpCAM), oregovomab (anti-CA-125), otlertuzumab (anti-CD37), pankomab (anti-tumor specific glycosylation of MUC1), parsatuzumab (anti-EGFL7), pascolizumab (anti-IL-4), patritumab (anti-HER3), pemtumomab (anti-MUC1), pertuzumab (anti-HER2/neu), pidilizumab (anti-PD-1), pinatuzumab vedotin (anti-CD22), pintumomab (anti-adenocarcinoma antigen), polatuzumab vedotin (anti-CD79B), pritumumab (anti-vimentin), PRO131921 (anti-CD20), quilizumab (anti-IGHE), racotumomab (anti-N-glycolylneuraminic acid), radretumab (anti-fibronectin extra domain-B), ramucirumab (anti-VEGFR2), rilotumumab (anti-HGF), robatumumab (anti-IGF-1 receptor), roledumab (anti-RHD), rovelizumab (anti-CD11 & CD18), samalizumab (anti-CD200), satumomab pendetide (anti-TAG-72), seribantumab (anti-ERBB3), SGN-CD19A (anti-CD19), SGN-CD33A (anti-CD33), sibrotuzumab (anti-FAP), siltuximab (anti-IL-6), solitomab (anti-EpCAM), sontuzumab (anti-episialin), tabalumab (anti-BAFF), tacatuzumab tetraxetan (anti-alpha-fetoprotein), taplitumomab paptox (anti-CD 19), telimomab aritox, tenatumomab (anti-tenascin C), teneliximab (anti-CD40), teprotumumab (anti-CD221), TGN1412 (anti-CD28), ticilimumab (anti-CTLA-4), tigatuzumab (anti-TRAIL-R2), TNX-650 (anti-IL-13), tositumomab (anti-CS20), tovetumab (anti-CD140a), TRBS07 (anti-GD2), tregalizumab (anti-CD4), tremelimumab (anti-CTLA-4), TRU-016 (anti-CD37), tucotuzumab celmoleukin (anti-EpCAM), ublituximab (anti-CD20), urelumab (anti-4-1BB), vantictumab (anti-Frizzled receptor), vapaliximab (anti-AOC3 (VAP-1)), vatelizumab (anti-ITGA2), veltuzumab (anti-CD20), vesencumab (anti-NRP1), visilizumab (anti-CD3), volociximab (anti-integrin $\alpha 5\beta 1$), vorsetuzumab mafodotin (anti-CD70), votumumab (anti-tumor antigen CTAA16.88), zalutumumab (anti-EGFR), zanolimumab (anti-CD4), zatuximab (anti-HER1), ziralimumab (anti-CD147 (basigin)), RG7636 (anti-ETBR), RG7458 (anti-MUC16), RG7599 (anti-NaPi2b), MPDL3280A (anti-PD-L1), RG7450 (anti-STEAP1), and GDC-0199 (anti-Bcl-2).

The protein of interest may be expressed in any suitable plant host that is transformed by the nucleotide sequence, or constructs, or vectors as described herein. Examples of suitable hosts include, but are not limited to, plants form a genus selected from the group consisting of *Arabidopsis, Nicotiana, Brassica, Ipomoea, Zea, Sorghum, Carthamus, Glycine, Triticum, Solanum, Avena, Secale, Medicago, Helianthus, Gossypium, Hordeum, Oryza, Panax,* and *Pisum*. Such genera include agricultural crops, for example canola, *Brassica* spp., maize, *Nicotiana* spp., (tobacco) (e.g., *Nicotiana benthamiana*), alfalfa, potato, sweet potato (*Ipomoea batatus*), ginseng, pea, oat, rice, soybean, wheat, barley, sunflower, cotton, corn, rye (*Secale cereale*), sorghum (*Sorghum bicolor, Sorghum vulgare*), and safflower (*Carthamus tinctorius*).

In various implementations, incubating the plant may include modifying light supplied to the plant (or a portion of the plant), during growth of the plant. For example, incubating the plant may include modifying a duration of light supplied to the plant during one or more specified time periods (such as supplying twelve hours of light on a first day and then supplying fourteen hours of light on a second day), modifying an intensity of light as described above supplied to the plant, modifying a wavelength of light as described above supplied to the plant (such as using a first wavelength between 6:00 A.M. and 12:00 P.M., and a shorter second wavelength between 12:00 P.M. and 6:00 P.M., or different wavelengths during similar time periods on different days), etc.

The method may include sensing a level production of the protein of interest. The duration, intensity and/or wavelength of the light may be modified according to the sensed level of production of the protein of interest. Similarly, a level of growth of the plant may be sensed, and the duration, intensity and/or wavelength of the light may be modified according to the sensed level of growth of the plant.

Although duration, intensity and wavelength of light are provided by example above, other embodiments may modify any other suitable light parameter, or other suitable control parameter for the growth environment of the plant (such as an ambient temperature, a water level, a soil composition, a nutrient level, etc.). Also, other suitable plant parameters may be sensed in order to modify the control parameters.

In various implementations, the method may include using an artificial intelligence algorithm to calculate a modification value according to a sensed plant parameter, such as a level of growth or a level of production of a protein of interest. The duration, intensity and/or wavelength of light (or any other suitable control parameter), may then be modified according to the calculated at least one modification value. For example, the artificial intelligence algorithm may receive a sensed plant parameter as an input, and output a change to one or more control parameters of the growth environment of the plant.

The artificial intelligence algorithm may include any suitable algorithm, as explained further below. For example, the artificial intelligence algorithm may include a machine learning model trained to predict a growth of the plant, a production of the protein of interest, etc., based on a duration, intensity and/or wavelength of light (or any other suitable control parameter). The machine learning model may be trained according to historical values of plant growth, protein production, etc., based on multiple values of light durations, intensities, wavelengths or other suitable control parameters.

The level of growth of the plant, the production of the protein of interest, etc., may be determined using at least one sensor associated with the plant. Any suitable sensor may be used, such as a dendrometer, a strain sensor, a light sensor, a temperature sensor, a moisture sensor, a camera, etc.

C. Medium Amendment

As used herein, a "medium" or "media" refers to a material in which plants grow. The functions of a plant medium may include holding water, holding and exchanging nutrients, gas exchange, and root anchoring. Plant media types include soil, peat moss, coconut coir, bark chips, rice hulls, wood fiber, clay pebbles, rock wool, stones, gravel, plastic foam, perlite, vermiculite, pumice, sand, hydrogel etc. Plant media may also be water based and may include a gelling agent such as agar, Phytagel™, Gellan Gum (Gellan), etc. In any embodiment, the medium or media may be soil.

As used herein, a "medium amendment" refers a material that is added to the medium (e.g., soil) for the purpose of improving its physical, chemical and/or biological characteristics and/or providing one or more nutrients to plants as well as for improving protein production in a plant or a part of a plant. As used herein, "amending a medium" refers to adding a suitable material to a medium (e.g., soil) in order to improve its physical, chemical and/or biological characteristics and/or provide it with one or more nutrients. In any embodiment, the medium amendment may be a soil amendment.

In any embodiment, the medium amendment includes a calcium carbonate ($CaCO_3$) source including aragonite. Aragonite, a natural orthorhombic crystalline form of calcium carbonate, occurs most commonly in beds of gypsum and of iron ore. Aragonite differs from calcite in that is has an orthorhombic crystalline structure, a greater specific gravity (2.93 to 2.95 $g/cm^3$ as compared to 2.71 $g/cm^3$ for calcite), and less distinct cleavage than calcite.

One form of aragonite, known as "oolitic aragonite," occurs on the ocean floor throughout the world. Oolitic aragonite occurs in discrete grains, which are essentially spherical in form. The material as a marine deposit is unconsolidated and varies in grain size with varying amounts of shell fragments intermixed therein. Oolitic aragonite can be found in the Caribbean, for example, on and around the Bahama islands. An exemplary composition of oolitic aragonite is provided in Table 1 below.

TABLE 1

| Composition | Percent by Weight |
|---|---|
| $CaCO_3$ | 97.00 |
| $SiO_2$ | 0.04 |
| $Fe_2O_3$ | 0.02 |
| $Al_2O_3$ | 0.02 |
| MgO | 0.23 |
| Mn | 0.0005 to 0.005 |
| Sr | 0.1 to 1.0 |
| S (organic) | 0.13 |
| S (inorganic) | 0.01 |
| Chloride (as NaCl) | 0.25 |
| Other organic matter | 0.41 |

Oolitic aragonite may be recovered from the ocean floor, for example, by dredging or otherwise removing the oolitic aragonite from the ocean floor. Dredging of the ocean floor can take place near, adjacent to, or at a beach in the Bahamas Islands. The recovered oolitic aragonite can include various sizes of material. In any embodiment, the recovered oolitic aragonite can have a particular size diameter from about 50 µm to about 2 mm. In some embodiments, oolitic aragonite can first be screened to remove any oversized material, such as shell fragments having a particle size diameter greater than or equal to about 275 µm. Alternatively, oolitic aragonite can be used directly from the ocean without any screening, grinding, or both. In other words, the oolitic aragonite can be unprocessed when incorporated into a composition or medium, such as soil. Thus, the term "unprocessed" as used herein, means no further treatment to the aragonite after its recovery from the ocean floor other than the mere handling and transport of it to a stock pile and then admixing with a component. In any embodiment, the oolitic aragonite is substantially dry, for example, containing about 10% or less moisture, prior to incorporation into a soil amendment.

In some embodiments, at least a portion of or substantially all of the oolitic aragonite may be ground prior to incorporation into a soil amendment, for example, in a ball mill. Suitable milling techniques and milled oolitic particles are described in US 2020/0308015, filed on 26 Apr. 2019, the entire contents of which are herein incorporated by reference in its entirety. The oolitic aragonite may be ground to oolitic particles having a diameter of greater than or equal to about 1 µm, greater than or equal to about 3 µm, greater than or equal to about 5 µm, greater than or equal to about 8 µm, greater than or equal to about 10 µm, greater than or equal to about 13 µm, greater than or equal to about 15 µm, greater than or equal to about 18 µm, or about 20 µm; or from about 1 µm to about 20 µm, about 1 µm to about 15 µm, about 3 µm to about 10 µm, about 3 µm to about 8 µm, or about 3 µm to about 5 µm.

Additionally or alternatively, the calcium carbonate source may further include calcic lime, dolomitic lime (calcium-magnesium carbonate, $CaCo_3+MgCO_3$), foundry residues, cement manufacturing residues, and combinations thereof.

In any embodiment, the calcium carbonate source (e.g., aragonite) may be present in the medium amendment, based on total weight of the medium amendment, in an amount of greater than or equal to about 1 wt %, greater than or equal to about 5 wt %, greater than or equal to about 10 wt %, greater than or equal to about 15 wt %, greater than or equal to about 20 wt %, greater than or equal to about 25 wt %, greater than or equal to about 30 wt %, greater than or equal to about 40 wt %, greater than or equal to about 50 wt %, or about 60 wt %; or from about 1 wt % to about 60 wt %, about 1 wt % to about 30 wt %, about 1 wt % to about 20 wt %, about 1 wt % to about 10 wt %, about 5 wt % to about 60 wt %, about 5 wt % to about 50 wt %, about 5 wt % to about 30 wt %, about 5 wt % to about 20 wt %, about 5 wt % to about 10 wt %, about 10 wt % to about 30 wt %, or about 10 wt % to about 20 wt %.

Additionally, the medium amendment may comprise one or more further components.

Examples of further components include, but are not limited to, a binding agent, an organic material, compost, gypsum, borax, weathered lignite, phosphate, paramagnetic basalt powder, glacial gravel dust, potassium, fulvic acid powder, humic acid powder, a filler, an herbicide, a pesticide, a fungicide, fungus, and a bacteria.

Any suitable binding agent for use in soil amendments may be used. For example, any non-toxic water-soluble binding agent known in the arts of agriculture, fertilizers, alimentation, and/or mining may be used. More specifically, calcium or sodium lignosulphonate compounds, such as LIGNOSOL™ may be used. Also, honey, molasses or any binder solution compatible with ecologic uses with high solubility in water may be used.

Organic materials may include manure of different animals, such as cows, pigs, horses, hens and others, and may be used as a starting material. Also, organic material may include any organic sludge (e.g., municipal, slaughterhouse, etc.), wood residues, industrial organic residues, crops residues, etc.

As used herein, "compost" refers to an organic material comprising decomposed or partially decomposed remnants of organic materials resulting from the break-down of these materials by bacteria, fungi, and other organisms, i.e. from the composting process. In any embodiment, the compost may have a carbon to nitrogen (C/N) ratio between about 1 and about 13. The compost may be prepared by any methods known in the art. For example, it may be prepared "naturally" in free air, in an aerobic reactor, in an anaerobic reactor or any combination of these methods. The starting materials used for preparing the compost may be any material known by those of skill in the art to be compostable or digestible. For example, any material that is putrescible may be used as a starting material. Also any digestible or partly digested organic materials as described above can be used to prepare the compost used in the present invention.

Examples of fillers (also referred to as an inert carrier) include, but are not limited to, a starch, a modified starch, maltodextrin, gum, diatomaceous earth, loam, a cellulose, biochar, pumice, silica, natural or synthetic silicates, silica, resins, waxes, solid fertilizers (for example ammonium salts), talc, kaolins, limestone, lime, quartz, chalk, clay (e.g., mectites, hectorites, bentonites, montmorillonites, celites, illites and combinations thereof), attapulgite, dolomite, a zeolite, perlite, diatomaceous earths, vermiculite, humus, activated charcoal, various phosphorous compounds, and combinations thereof.

Pesticides, such as fungicides and/or herbicides may be included in the soil amendment. The pesticides may include compounds that act only below the ground. Examples of fungicides include, but are not limited to, as captan, thiram, metalaxyl, fludioxonil, oxadixyl, and isomers of each of those materials, and the like. Examples of herbicides include, but are not limited to, compounds selected from glyphosate, carbamates, thiocarbamates, acetamides, triazines, dinitroanilines, glycerol ethers, pyridazinones, uracils, phenoxys, ureas, and benzoic acids; herbicidal safeners such as benzoxazine, benzhydryl derivatives, N,N-diallyl dichloroacetamide, various dihaloacyl, oxazolidinyl and thiazolidinyl compounds, ethanone, naphthalic anhydride compounds, and oxime derivatives; chemical fertilizers; and biological fertilizers.

Examples of bacteria include, but are not limited to, bacteria of the following genera: *Achromobacter, Acinetobacter, Aeromonas, Agrobacterium, Ampelomyces, Aureobasidium, Azospirillum, Azotobacter, Bacillus, Beauveria, Bradyrhizobium, Burkholderia, Candida, Chaetomium, Chromobacterium, Chryseobacterium, Chryseomonas, Cordyceps, Cryptococcus, Dabaryomyces, Delftia, Erwinia, Exophilia, Gliocladium, Herbaspirillum, Lactobacillus, Mariannaea, Microccocus, Mitsuaria, Paecilomyces, Paenibacillus, Pantoea, Photorhabdus, Phytobacter, Pichia, Pseudomonas, Pseudacidovorax, Rhizobium, Saccharomyces, Sporobolomyces, Stenotrophomonas, Streptomyces, Talaromyces, Trichoderma*, Xenorhabdus, and combinations thereof.

Examples of fungi include, but are not limited to, *Muscodor* species, *Aschersonia aleyrodis, Beauveria bassiana* ("white muscarine"), *Beauveria brongniartii, Chladosporium herbarum, Cordyceps clavulata, Cordyceps entomorrhiza, Cordyceps facis, Cordyceps gracilis, Cordyceps melolanthae, Cordyceps militaris, Cordyceps myrmecophila, Cordyceps ravenelii, Cordyceps sinensis, Cordyceps sphecocephala, Cordyceps subsessilis, Cordyceps unilateralis, Cordyceps variabilis, Cordyceps washingtonensis, Culicinomyces clavosporus, Entomophaga grylli, Entomophaga maimaiga, Entomophaga muscae, Entomophaga praxibulli, Entomophthora plutellae, Fusarium lateritium, Hirsutella citriformis, Hirsutella thompsoni, Metarhizium anisopliae* ("green muscarine"), *Metarhizium flaviride, Muscodor albus, Neozygitesfloridana, Nomuraea rileyi, Paecilomyces farinosus, Paecilomyces fumosoroseus, Pandora neoaphidis, Tolypocladium cylindrosporum, Verticillium lecanii, Zoophthora radicans*, mycorrhizal species, such as Laccaria bicolor, and combinations thereof.

In any embodiment, the one or more further components may be present in the medium amendment, singularly or in combination, based on total weight of the medium amendment, in an amount of greater than or equal to about 1 wt %, greater than or equal to about 10 wt %, greater than or equal to about 20 wt %, greater than or equal to about 40 wt %, greater than or equal to about 50 wt %, greater than or equal to about 60 wt %, greater than or equal to about 70 wt %, greater than or equal to about 80 wt %, greater than or equal to about 90 wt %, greater than or equal to about 95 wt %, or about 99 wt %; or from about 1 wt % to about 99 wt %, about 10 wt % to about 99 wt %, about 20 wt % to about 99 wt %, about 40 wt % to about 99 wt %, about 40 wt % to about 95 wt %, about 40 wt % to about 90 wt %, about 40 wt % to about 80 wt %, about 40 wt % to about 60 wt %, about 60 wt % to about 99 wt %, about 60 wt % to about 90 wt %, about 60 wt % to about 80 wt %, about 80 wt % to about 99 wt %, about 80 wt % to about 95 wt %, about 80 wt % to about 90 wt %, about 90 wt % to about 99 wt %, 90 wt % to about 95 wt %, or about 95 wt % to about 99 wt %.

As used herein, "medium environment" refers to the medium, such as soil, in which the plant is present within, for example, the medium in which the seed is planted as well as the medium adjacent to and surrounding the roots, leaves, and stem or stalk of the plant. It is contemplated herein that the medium amendment may be applied to the medium environment in a variety of forms in order for the composition to be readily absorbed by the medium and improve the medium quality. For example, the medium amendment can be prepared in dry form, such as a loose meal or granular form. Alternatively, the medium amendment can be prepared in liquid form by steeping large mesh bags of the soil improving composition in water. The medium amendment can also be used with a pearlizer to form small pearls.

The amount of medium amendment that may be added to a medium environment can and will vary depending upon physical and chemical conditions of the medium, the moisture conditions of the medium, and the plants to be grown in the medium. For example, the medium amendment may be used in an amount of between about 200 lbs per acre and about 750 lbs per acre, between about 300 lbs per acre and about 600 lbs per acre, or about 500 lbs per acre. In some embodiments, where the medium amendment is prepared in liquid form, the medium amendment may be applied to the medium (e.g., soil) in an amount of between about 0.5 gal per acre and about 15 gal/acre, between about 1 gal per acre and about 10 gal per acre, or between about 1 gal per acre and about 5 gal per acre.

In any embodiment, the medium amendment may be added to the medium environment before, during, after seeding, or a combination thereof. It is contemplated herein that the medium amendment may be add once or multiple times (two times, three times, four times, five times, ten times, etc.) to the medium environment. The medium amendment can be added to the medium using seeding equipment, spreaders, or any other type of equipment able to handle granulated amendments and/or fertilizers commonly known in the art. A chemical fertilizer, a mineral fertilizer, another medium amendment, or a mixture thereof, may be added to the soil before, after, or while the medium amendment is being added to the medium environment. Alternatively, the chemical fertilizer, mineral fertilizer, other medium amendment or mixture thereof may be mixed with the soil amendment prior to adding to the medium environment.

D. Optional Further Steps

The method may further include harvesting of the plant or a portion of the plant. For example, the whole plant comprising leaves and stems may be harvested or only plant leaves may be harvested.

Additionally, the protein of interest produced according to the methods described herein may be purified, partially purified from a plant, portion of a plant or plant matter, or may be administered as an oral vaccine, using methods as known to one of skill in the art. Purification may include production of an apoplast fraction as described in WO 2011/035422 (which is incorporated herein by reference in its entirety). For preparative size exclusion chromatography, a preparation comprising the protein of interest may be obtained and insoluble material removed by centrifugation. Precipitation with PEG may also be used. The recovered protein may be quantified using conventional methods (for example, Bradford Assay, BCA), and the extract passed through a size exclusion column, using for example SEPHACRYL™, SEPHADEX™, or similar medium, and the fractions collected. Blue Dextran 2000 or a suitable protein, may be used as a calibration standard. The extract may also be passed through a cation exchange column and active fractions collected. Following chromatography, fractions may be further analyzed by protein electrophoresis, immunoblot, or both, to confirm the presence of the protein of interest and the protein complement of the fraction.

By the term "minimal processing" it is meant plant matter, for example, a plant or portion thereof comprising a protein of interest which is partially purified to yield a plant extract, homogenate, fraction of plant homogenate or the like (i.e., minimally processed). Partial purification may comprise, but is not limited to disrupting plant cellular structures thereby creating a composition comprising soluble plant components, and insoluble plant components, which may be separated for example, but not limited to, by centrifugation, filtration or a combination thereof. In this regard, proteins secreted within the extracellular space of leaf or other tissues could be readily obtained using vacuum or centrifugal extraction, or tissues could be extracted under pressure by passage through rollers or grinding or the like to squeeze or liberate the protein free from within the extracellular space. Minimal processing could also involve preparation of crude extracts of soluble proteins, since these preparations would have negligible contamination from secondary plant products. Further, minimal processing may involve aqueous extraction of soluble protein from leaves, followed by precipitation with any suitable salt. Other methods may include large scale maceration and juice extraction in order to permit the direct use of the extract.

It is contemplated herein that the methods described herein encompass modifying the expression of a protein of interest in a plant or a portion thereof, for example, a protein already produced in the plant. Modifying the expression of a protein of interest may include increasing and/or decreasing protein production, silencing the gene, etc.

Also provided herein are transgenic plants, plant cells or seeds containing the gene construct of the present disclosure that may be used as a platform plant suitable for transient protein expression described herein. Methods of regenerating whole plants from plant cells are also known in the art (for example see Guerineau and Mullineaux (1993, Plant transformation and expression vectors. In: Plant Molecular Biology Labfax (Croy RRD ed) Oxford, BIOS Scientific Publishers, pp 121-148; incorporated herein by reference in its entirety). In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations, either from seeds or using vegetative propagation techniques. Transgenic plants can also be generated without using tissue culture. Methods for stable transformation, and regeneration of these organisms are established in the art and known to one of skill in the art. Available techniques are reviewed in Vasil et al., (Cell Culture and Somatic Cell Genetics of Plants, Vol I, I1 and III, Laboratory Procedures and Their Applications, Academic Press, 1984), and Weissbach and Weissbach, (Methods for Plant Molecular Biology, Academic Press, 1989), both of which are incorporated herein by reference in their entirety.

II. Systems for Producing a Protein of Interest

FIG. 3 illustrates a block diagram of an example system 202, which may be used for producing a protein of interest within a plant or a portion of a plant. For example, a medium environment as described herein may be adapted to grow a plant, where the medium environment includes a medium amendment as described herein such as, e.g., a calcium carbonate source comprising aragonite. The plant may include one or more nucleic acids introduced into the plant or the portion of the plant, where the nucleic acid includes, for example, a nucleotide sequence encoding the protein of interest, and the nucleotide sequence is operatively linked to a regulatory region.

Incubation equipment may be adapted to incubate the plant under conditions that permit the expression of the nucleotide sequence encoding the protein of interest, thereby producing the protein of interest. For example, the incubation equipment may include at least one lighting element to supply light to the plant. A sensor may be associated with the plant and configured to sense at least one parameter of the plant.

Figure 7:
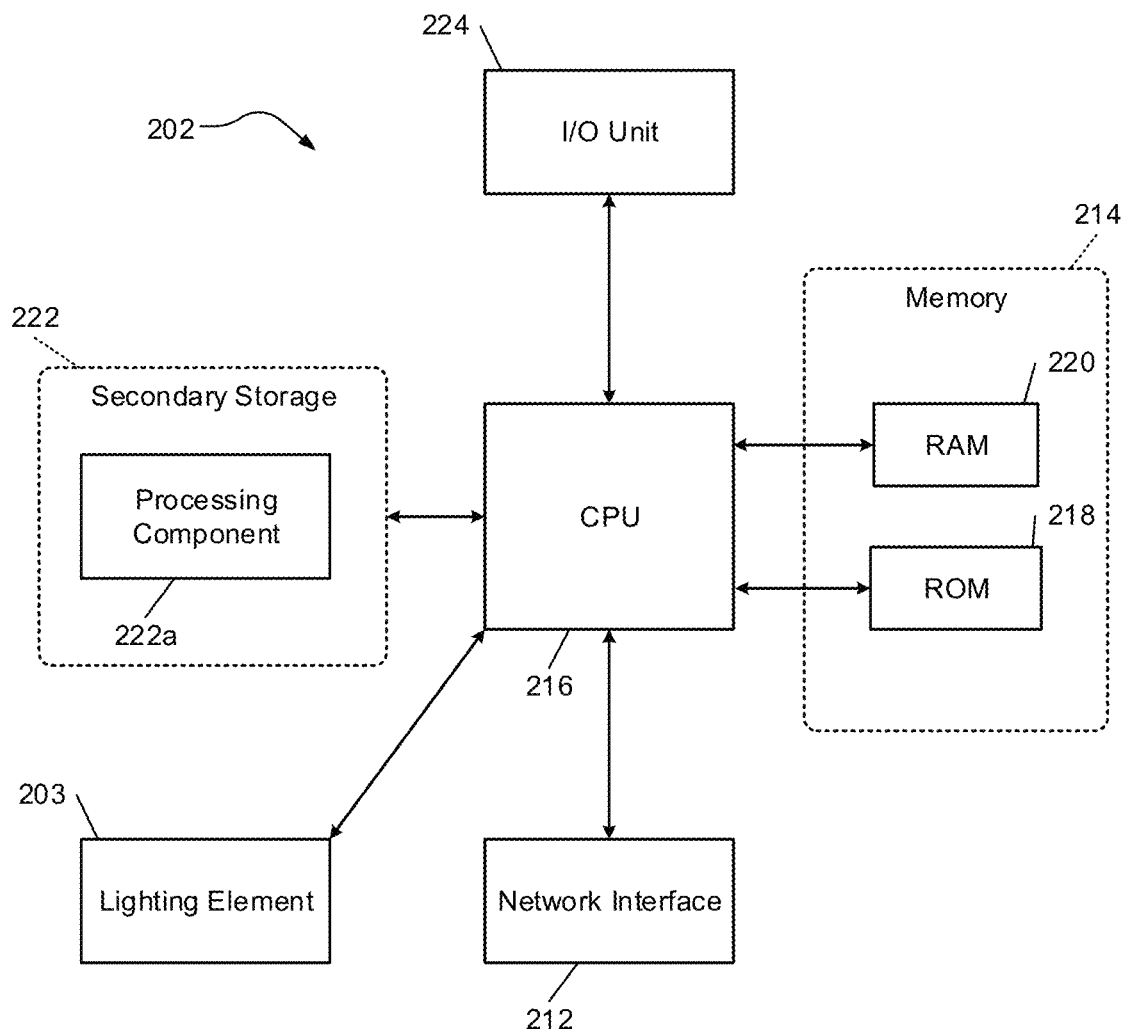
FIG. 7 is a functional block diagram of an example system for producing a protein of interest within a plant or a portion of the plant.

The system 202 may be configured to control operation of one or more aspects of the system, such as a lighting element 203. As shown in FIG. 7, the system 202 includes one or more processors 216 (which may be referred to as a central processor unit or CPU) that is in communication with memory 214 including optional read only memory (ROM) 218 and optional random access memory (RAM) 220, and optional secondary storage 222 (such as disk drives). The processor 216 may be implemented as one or more CPU chips. The system 202 further includes optional input/output (I/O) devices 224, and network connectivity devices (e.g., a communication interface) 212.

In various implementations, the memory 214 may be configured to store computer-executable instructions, and the one or more processors 216 may be configured to execute the instructions control operation of the lighting element 203. One or more of the of the I/O devices 224 may include a sensor associated with the plant and configured to sense at least one parameter of the plant.

The instructions may include receiving the at least one parameter of the plant as detected by the sensor, and implementing one or more control operations according to the at least one parameter. For example, the one or more processors 216 may be configured to control operation of the lighting element 203 to modify a duration of light supplied to the plant during one or more specified daily time periods, during growth of the plant, according to the sensed at least one parameter of the plant.

Alternatively, or in addition, the one or more processors 216 may be configured to control operation of the lighting element 203 to modify an intensity of light supplied to the plant during growth of the plant, according to the sensed at least one parameter of the plant. As another option, the one or more processors may be configured to control operation of the lighting element 203 to modify a wavelength of light supplied to the plant during growth of the plant, according to the sensed at least one parameter of the plant.

The sensed parameter may be used to control operation of the lighting element 203 in any suitable manner. For example, the one or more processors 216 may be configured to determine a level of production of the protein of interest according to the sensed at least one parameter of the plant, to determine a level of growth of the plant according to the sensed at least one parameter of the plant, etc.

The determined values may then be used to control the duration, intensity, wavelength, etc., of the lighting element 203. For example, the determined level of growth of the plant or determined level of production of the protein interest may be used to modify the duration, intensity, wavelength, etc., of the lighting element 203. In various implementations, lower levels of determined plant growth may cause the one or more processors 216 to increase a duration or intensity of the lighting element 203 to promote growth, lower levels of protein production may cause the one or more processors 216 to adjust a wavelength of the lighting element 203 to a value that is more conducive to production of the protein of interest, etc.

Although the above description provides examples of controlling duration, intensity and/or wavelength of the light, various implementations may control other aspects of lighting for the plant, or any other suitable components that facilitate growth of the plant or production of the protein of interest. For example, one or more of the I/O devices 224 may include a water element or suppling water to the plant, a thermal element for controlling an ambient temperature adjacent the plant, a nutrition element for controlling dispersion of food or chemicals to the plant or the soil environment of the plant, etc.

Similarly, the I/O devices 224 may include any suitable sensors, such as a dendrometer, a strain sensor, a light sensor, a temperature sensor, a moisture sensor a camera, etc. This sensors may be used to detect or determine growth of the plant, protein production of the plant, or any other suitable parameter of the plant that may be desirable for controlling operation of lighting elements, etc., associated with the plant.

In various implementations, the memory 214 may be configured to store an artificial intelligence algorithm. The one or more processors 216 may be configured to use the artificial intelligence algorithm to calculate at least one modification value based on a sensed or determined parameter, and control operation of the lighting element 203, etc., based on the modification value. For example, the one or more processors 216 may supply a determined or sensed level of growth of the plant to the artificial intelligence algorithm, in order to determine a modification value such as increasing or decreasing a duration of lighting. The one or more processors 216 may then control the lighting element 203 to increase or decrease the duration of supplied light during a next time period cycle, according to the calculated modification value.

The artificial intelligence algorithm may include any suitable algorithm, such as a machine learning model. For example, a machine learning model may trained to predict optimal light duration, light intensity, light wavelength (or any other suitable control parameters) to promote growth of the plant or production of the protein of interest (or any other suitable plant parameters), according to historical values. The historical values may indicate levels of tested plant growth, protein production, etc., based on multiple values of light durations, light intensities, light wavelengths, etc.

Any suitable machine learning models may be used, and the models may be trained in any suitable fashion. For example, historical data may be separated into training data and test data, where the training data is used to train the model, and the test data is used to test model performance and prediction accuracy. Typically, the set of training data is selected to be larger than the set of test data, depending on the desired model development parameters. Separating a portion of the acquired data as test data allows for testing of the trained model against actual historical output data, to facilitate more accurate training and development of the model. This arrangement may allow the system to simulate an outcome of the machine learning prediction when it processes a new plant growth parameter, protein production parameter, etc., in the future. The model may be trained using any suitable machine learning model techniques, including those described herein, such as random forest, logistic regression, decision tree (for example, a light gradient boosted tree), and neural networks.

The trained model may be tested using the test data, and the results of the output data from the tested model may be compared to actual historical outputs of the test data, to determine a level of accuracy. The model results may be evaluated using any suitable machine learning model analysis, such as cumulative gain and lift charts. Lift is a measure of the effectiveness of a predictive model calculated as the ratio between the results obtained with and without the predictive model (for example, by comparing the tested model outputs to the actual outputs of the test data). Cumulative gains and lift charts provide visual aids for measuring model performance. Both charts include a lift curve and a baseline, where a greater area between the lift curve and the base line indicates a stronger model.

After evaluating the model test results, the model may be deployed if the model test results are satisfactory. Deploying the model may include using the model to make predictions for a large-scale input dataset with unknown outputs, and using the model to modify settings of elements that control the incubation environment of the plant. If the evaluation of the model test results is unsatisfactory, the model may be developed further using different parameters, using different modeling techniques, or using other model types.

One example machine learning model is a recurrent neural-network-based model, which may be to directly predict dependent variables without casting relationships between the variables into mathematical form. The neural network model includes a large number of virtual neurons operating in parallel and arranged in layers. The first layer is the input layer and receives raw input data. Each successive layer modifies outputs from a preceding layer and sends them to a next layer. The last layer is the output layer and produces output of the system.

In some embodiments, a convolutional neural network may be implemented. Similar to LSTM neural networks, convolutional neural networks include an input layer, a hidden layer, and an output layer. However, in a convolutional neural network, the output layer includes one fewer output than the number of neurons in the hidden layer and each neuron is connected to each output. Additionally, each input in the input layer is connected to each neuron in the hidden layer.

In various implementations, each input node in the input layer may be associated with a numerical value, which can be any real number. In each layer, each connection that departs from an input node has a weight associated with it, which can also be any real number. In the input layer, the number of neurons equals number of features (columns) in a dataset. The output layer may have multiple continuous outputs.

As mentioned above, the layers between the input and output layers are hidden layers. The number of hidden layers can be one or more (one hidden layer may be sufficient for many applications). A neural network with no hidden layers can represent linear separable functions or decisions. A neural network with one hidden layer can perform continuous mapping from one finite space to another. A neural network with two hidden layers can approximate any smooth mapping to any accuracy.

The number of neurons can be optimized. At the beginning of training, a network configuration is more likely to have excess nodes. Some of the nodes may be removed from the network during training that would not noticeably affect network performance. For example, nodes with weights approaching zero after training can be removed (this process is called pruning). The number of neurons can cause underfitting (inability to adequately capture signals in dataset) or over-fitting (insufficient information to train all neurons; network performs well on training dataset but not on test dataset).

Various methods and criteria can be used to measure performance of a neural network model. For example, root mean squared error (RMSE) measures the average distance between observed values and model predictions. Coefficient of Determination (R2) measures correlation (not accuracy) between observed and predicted outcomes. This method may not be reliable if the data has a large variance. Other performance measures include irreducible noise, model bias, and model variance. A high model bias for a model indicates that the model is not able to capture true relationship between predictors and the outcome. Model variance may indicate whether a model is not stable (a slight perturbation in the data will significantly change the model fit).

Referring again to FIG. 7, the secondary storage 222 may include one or more disk drives or tape drives. The secondary storage 222 may be used for non-volatile storage of data and as an over-flow data storage device if RAM 220 is not large enough to hold all working data. The secondary storage 222 may be used to store programs which are loaded into RAM 220 when such programs are selected for execution. In this embodiment, the secondary storage 222 has a processing component 222a comprising non-transitory instructions operative by the processor 216 to perform various operations of the methods of the present disclosure. The ROM 218 is used to store instructions and perhaps data which are read during program execution. The secondary storage 222, the memory 214, the RAM 220, and/or the ROM 218 may be referred to in some contexts as computer readable storage media and/or non-transitory computer readable media.

The optional I/O devices 224 may include printers, video monitors, liquid crystal displays (LCDs), plasma displays, touch screen displays, keyboards, keypads, switches, dials, mice, track balls, voice recognizers, card readers, paper tape readers, or other suitable input devices.

The network connectivity devices 212 may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards. The devices 212 may promote radio communications using protocols, such as code division multiple access (CDMA), global system for mobile communications (GSM), long-term evolution (LTE), worldwide interoperability for microwave access (WiMAX), near field communications (NFC), radio frequency identity (RFID), and/or other air interface protocol radio transceiver cards, and other suitable network devices. These network connectivity devices 212 may enable the processor 216 to communicate with the Internet and/or one or more intranets. With such a network connection, it is contemplated that the processor 216 might receive information from the network, might output information to the network in the course of performing the above-described method operations, etc. Such information, which is often represented as a sequence of instructions to be executed using processor 216, may be received from and outputted to the network, for example, in the form of a computer data signal embodied in a carrier wave.

The processor 216 executes instructions, codes, computer programs, scripts which it accesses from hard disk, floppy disk, optical disk (these various disk based systems may all be considered secondary storage 222), flash drive, memory

214, ROM 218, RAM 220, the network connectivity devices 212, etc. While only one processor 216 is shown, multiple processors may be present. Thus, while instructions may be discussed as executed by a processor, the instructions may be executed simultaneously, serially, or otherwise executed by one or multiple processors.

Although the system 202 is described with reference to a computing device, it should be appreciated that the system may be formed by two or more computing devices in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a dataset by the two or more computers.

In an embodiment, virtualization software may be employed by the system 202 to provide the functionality of a number of servers that is not directly bound to the number of computers in the system 202. The functionality disclosed above may be provided by executing an application and/or applications in a cloud computing environment). Cloud computing may include providing computing services via a network connection using dynamically scalable computing resources. A cloud computing environment may be established by an enterprise and/or may be hired on an as-needed basis from a third party provider.

It is understood that by programming and/or loading executable instructions onto the system 202, at least one of the CPU 216, the memory 214, the ROM 218, and the RAM 220 are changed, transforming the system 202 in part into a specific purpose machine and/or apparatus having the novel functionality taught by the present disclosure. It is fundamental to the electrical engineering and software engineering arts that functionality that can be implemented by loading executable software into a computer can be converted to a hardware implementation by well-known design rules.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. The phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are IEEE Standard 802.15.4 (including the ZIGBEE standard from the ZigBee Alliance) and, from the Bluetooth Special Interest Group (SIG), the BLUETOOTH wireless networking standard (including Core Specification versions 3.0, 4.0, 4.1, 4.2, 5.0, and 5.1 from the Bluetooth SIG).

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

The term "about", unless otherwise indicated, when used in conjunction with a numeral refers to a range spanning +/−10%, inclusive, around that numeral. For example, the term 'about 10 μm refers to a range of 9 to 11 μm, inclusive.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context.

The use of any and all examples, or exemplary language (e.g. "such as") provided with respect to certain embodiments herein is intended merely to better illuminate the invention and is not intended to pose a limitation on the embodiments disclosed herein. No language in the specification should be construed as indicating any non-claimed element essential to the practice of the invention.

It should be apparent to those skilled in the art that many more modifications besides those already described are possible. The systems, methods and devices disclosed herein are not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method for producing a protein of interest within a plant or a portion of a plant comprising:
 a) introducing one or more nucleic acids into the plant or the portion of the plant, the nucleic acid comprising a nucleotide sequence encoding the protein of interest and operatively linked to a regulatory region;
 b) incubating the plant or the portion of the plant under conditions that permit expression of the nucleotide sequence encoding the protein of interest, thereby producing the protein of interest; and
 c) adding a medium amendment to a medium environment of the plant, wherein the medium amendment comprises a calcium carbonate source comprising aragonite,
 wherein the protein of interest is nogapendekin-alfa-inbakicept (NAI), a heterodimeric bifunctional fusion complex comprising a soluble TGF-BRII domain and an IL-15/IL15RαSu domain linked by a tissue factor linker, a TxM, or a mAb; and
 wherein the plant is from a genus selected from the group consisting of *Arabidopsis, Nicotiana, Brassica, Ipomoea, Zea, Sorghum, Carthamus, Glycine, Triticum, Solanum, Avena, Secale, Medicago, Helianthus, Gossypium, Hordeum, Oryza, Panax,* and *Pisum.*

2. The method of claim 1, wherein the heterodimeric bifunctional fusion complex comprising a soluble TGF-βRII domain and an IL-15/IL15RαSu domain linked by a tissue factor linker is HCW9218 or HCW9228.

3. The method of claim 1, wherein the TxM is a complex comprising an IL-15N72D:IL-15RαSu/Fc scaffold linked to a binding domain.

4. The method of claim 3, wherein the binding domain recognizes an immune checkpoint molecule, immune signaling molecule, or a disease antigen.

5. The method of claim 1, wherein in step b), the nucleic acid is transiently expressed in the plant.

6. The method of claim 1, wherein in step b), the nucleic acid is stably expressed in the plant.

7. The method of claim 1, wherein the medium environment comprises soil.

8. The method of claim 1, wherein the aragonite is in the form of particles having a particle size of about 3 μm to about 10 μm in diameter.

9. The method of claim 1, wherein the aragonite is oolitic aragonite.

10. The method of claim 9, wherein the oolitic aragonite is unprocessed.

11. The method of claim 1, wherein the calcium carbonate source is present in the medium amendment in an amount of at least about 10 wt %, based on total weight of the medium amendment.

12. The method of claim 1, wherein the medium amendment further comprises one or more of: a binding agent, an organic material, compost, gypsum, borax, weathered lignite, phosphate, paramagnetic basalt powder, glacial gravel dust, potassium, fulvic acid powder, humic acid powder, a filler, an herbicide, a fungicide, fungus, and a bacteria.

13. The method of claim 1, wherein the medium amendment is added to the medium environment prior to seeding, during seeding, after seeding, or a combination thereof.

14. The method of claim 1, further comprising a step d) of harvesting the plant or the portion of the plant.

15. The method of claim 14, wherein the step d) further comprises purifying the protein of interest.

16. The method of claim 1, wherein incubating the plant includes at least one of:
modifying a duration of light supplied to the plant during one or more specified daily time periods, during growth of the plant;
modifying an intensity of light supplied to the plant during growth of the plant; and
modifying a wavelength of light supplied to the plant during growth of the plant.

17. The method of claim 16, further comprising determining a level of production of the protein of interest, wherein modifying the duration, intensity and/or wavelength of light includes modifying the duration, intensity, and/or wavelength of light according to the determined level of production of the protein of interest.

18. The method of claim 16, further comprising determining a level of growth of the plant, wherein modifying the duration, intensity, and/or wavelength of light includes modifying the duration, intensity and/or wavelength of light according to the determined level of growth of the plant.

19. The method of claim 17, wherein:
determining a level of growth of the plant and/or the production of the protein of interest includes determining the level of growth and/or production of the protein of interest using at least one sensor associated with the plant; and
the at least one sensor includes at least one of a dendrometer, a strain sensor, a light sensor, a temperature sensor, a moisture sensor, and a camera.

20. The method of claim 1, wherein the plant is from a *Nicotiana* genus.

* * * * *